United States Patent [19]

Yokobayashi et al.

[11] 4,200,693

[45] Apr. 29, 1980

[54] PROCESSES FOR PRODUCING GLUCAN USING ELSINOE

[75] Inventors: Koji Yokobayashi; Toshiyuki Sugimoto, both of Okayama, Japan

[73] Assignee: Kabushiki Kaisha Hayashibara Seibutsu Kagaku Kenkyujo, Okayama, Japan

[21] Appl. No.: 891,386

[22] Filed: Mar. 29, 1978

[30] Foreign Application Priority Data

Mar. 29, 1977 [JP] Japan .................................. 52/34946
Jul. 25, 1977 [JP] Japan .................................. 52/89038

[51] Int. Cl.$^2$ ...................... C12P 19/04; C12R 1/645
[52] U.S. Cl. ...................................... 435/101; 435/911
[58] Field of Search .................. 195/31 P, 81; 536/1; 435/101, 911

[56] References Cited

PUBLICATIONS

Wolf, et al., *The Fungi*, vol. I, John Wiley & Sons, Inc., New York, (1947) pp. 165–170.
Tanaka, et al., "Grape Anthrachose, Elsinoe ampelina,1, Cultural Aspects of the Fungus", *Chem. Abst.*, vol. 83, No. 11 (1975) abs # 93537g.

*Primary Examiner*—Thomas G. Wiseman
*Attorney, Agent, or Firm*—Browdy and Neimark

[57] ABSTRACT

A glucan characterized by repeating units of [3)-Glc-(1→4)-Glc-(1→4)-Glc-(1→] wherein Glc represents alpha-D-glucopyranose residue is produced by cultivating a microorganism of the genus Elsinoe capable of producing said glucan on a nutrient medium containing one or more members selected from the group consisting of various starch hydrolyzates, mannose, fructose, mannitol and xylose to produce said glucan in the medium, separating and recovering said glucan therefrom.

2 Claims, 2 Drawing Figures

PROCESSES FOR PRODUCING GLUCAN USING ELSINOE

FIELD OF THE INVENTION

The present invention relates to processes for producing a glucan (elsinan) comprising repeating units of [3)-Glc-(1→4)-Glc-(1→4)-Glc-(1→], (wherein Glc hereinafter represents alpha-D-glucopyranose residue, and to the glucan elsinan itself.

BACKGROUND OF THE INVENTION

The known polysaccharides comprising alpha-linked D-glucose, namely, alpha-glucan, include starch derived from plants, glycogen derived from animals, microbial dextran and microbial pullulan.

Although these alpha-glucans have been consumed in large amounts, their uses have been mainly directed to the food and pharmaceutical industries.

SUMMARY OF THE INVENTION

The object of the present invention is to develop a new glucan which is utilizable not only in the food and pharmaceutical industries but also in other various industrial fields. The present inventors discovered that the polysaccharide, obtainable by cultivating microorganisms of genus Elsinoe on a nutrient medium containing at least one or more members of a group consisting of starch hydrolyzates, mannose, fructose, mannitol and xylose as sugar sources, is a novel water-soluble glucan comprising repeating units of [3)-Glc-(1→4)-Glc-(1→4)-Glc-(1→] and has a number of industrial applications including those as various types of film. The inventors designated the novel glucan as elsinan.

DETAILED DESCRIPTION OF THE PREFERRED EMBODIMENTS

The elsinan was identified as alpha-glucan, based on the following properties.

Purity: No contaminants were detectable on subjection to ultracentrifugation and electrophoresis.

Element analysis: Measurements; C=4.41%, 44.5%, H=6.18%, 6.15%, N<0.1%, Ash<0.01%, Calculations; C=44.4%, H=6.17%

Specific rotation: $[\alpha]_D^{25}$ +175~280° (1=1, c=1.6, 0.5N-NaOH)

Solubility: Dissolves readily in water, 0.1N-NaOH, 90% formic acid, formamide, or dimethyl sulfoxide. Insoluble in organic solvents such as methanol, ethanol, acetone, chloroform, or ethyl acetate.

Appearance: A white, fine powder without taste or order.

Color reactions: Becomes green by the anthrone-sulfuric reaction. Becomes yellow by the cystein-sulfuric acid reaction. Remains colorless by the Morgan-Elson reaction. Iodine stain, negative.

Figure 1:
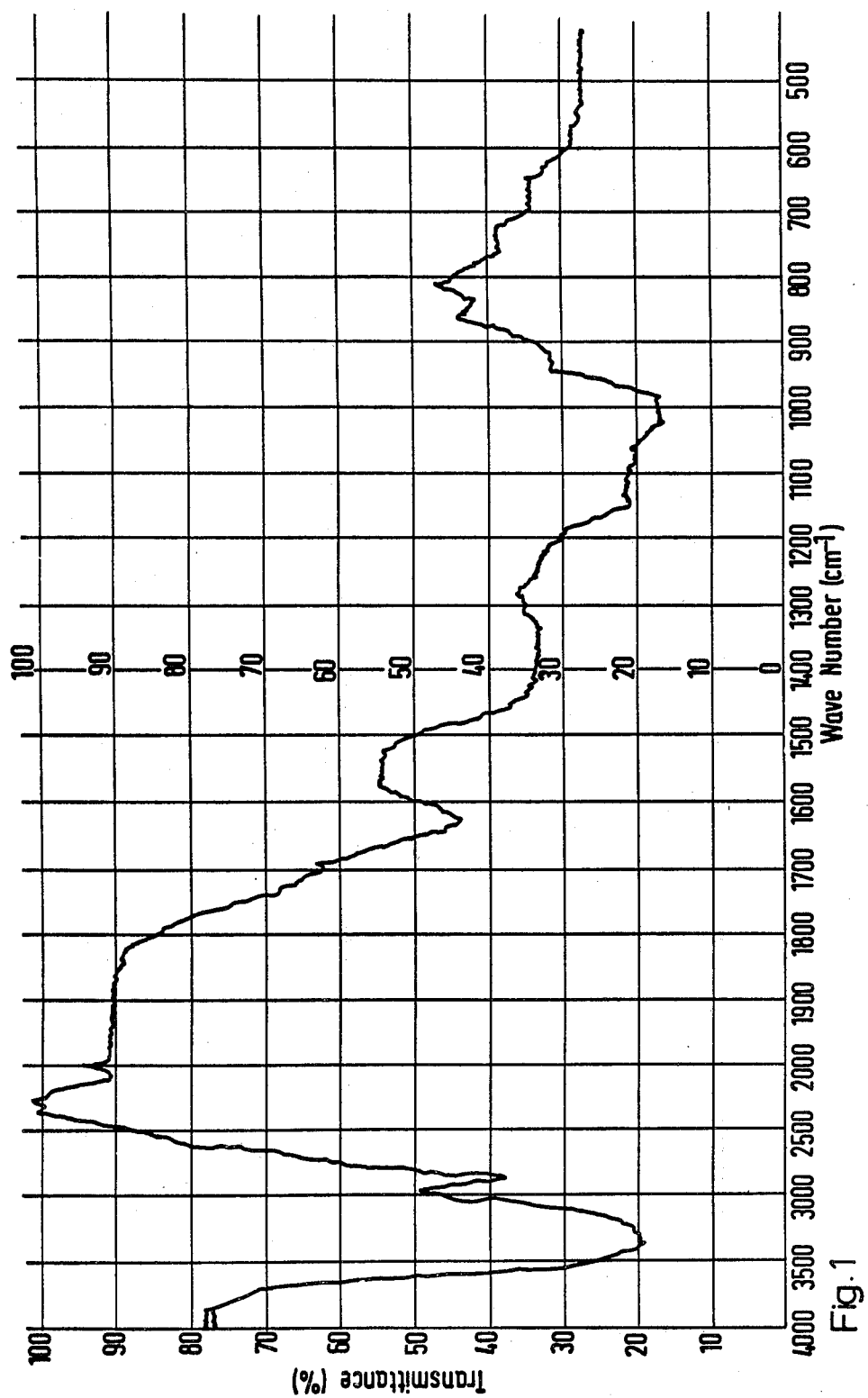
FIG. 1 shows the infrared spectrum of the purified elsinan.

Infrared spectrum: Infrared spectrum by the KBr tablet is given in FIG. 1. The absorbance at 840 $cm^{-1}$ in the infrared spectrum was characteristic of the alpha-type linkage.

Components: The analytical results obtained by paper chromatography, gas chromatography, liquid chromatography and glucose oxidase peroxidase method showed that the sugar obtained from hydrolyzing elsinan with 1N-sulfuric acid, 1N-hydrochloric acid or 1N-trichloroacetic acid was D-glucose.

In addition, the analytical results obtained by using chemical procedures such as methylation, periodate oxidation, Smith degradation and controlled Smith degradation show that the elsinan disclosed in the present invention is a novel glucan with an entirely new structure so far unknown. The novel glucan (elsinan) will be disclosed in further details.

(1) The high specific rotation, $[\alpha]_D^{25}$ +175~280°, and the absorbance at 840 $cm^{-1}$ in the infrared spectrum indicate that all or most of glucosidic linkages constructing elsinan are of alpha type.

(2) a. Qualitative and quantative analyses by gas chromatography and mass spectrum of the hydrolyzate of methylated elsinan show that the major components are 2,4,6-tri-O-methyl-D-glucose (ca. 30%) and 2,3,6-tri-O-methyl-D-glucose (ca. 68%), with small amounts of 2,4-di-O-methyl-D-glucose (ca. 1%) and 2,3,4,6-tetra-O-methyl-D-glucose (ca. 1%) present.

b. Complete oxidation of elsinan with periodate shows that 0.8 moles of periodate is consumed per glucose residue, with simultaneous formation of 0.07 moles of formic acid per glucose residue.

c. Qualitative and quantative analyses by paper chromatography, gas chromatography and liquid chromatography of the Smith degradation products of elsinan confirm that D-erythritol, 68~70%; D-glucose, 29~30%; glycerol, a trace.

The above results confirm that the glucose residues present in elsinan are essentially linear molecules comprising mainly alpha-1,4 and alpha-1,3 linkages in the molar ratio of 2.0~2.3: 1.0.

A very few of the glucose residues linked at the C-1 and C-3 positions with the adjacent glucose residues are branched at the C-6 position by alpha-1,6 linkage. Such glucose residue are, at most, one out of every 70 glucose residues.

(3) The analyses by paper chromatography and gas chromatography of controlled Smith degradation products of elsinan indicate that D-erythritol and 2-O-alpha-D-glucopyranosyl-D-erythritol are present in the molar ratio of 1.0~1.3:1.0 (the presence of 2-O-alpha-D-glucopyranosyl-D-erythritol indicates that the glucose residue is linked at the C-3 position by alpha-1,3 linkage with one adjacent glucose residue, and linked at the C-1 position by alpha-1,4 linkage with the adjacent glucose residue on the other side). In addition, a trace amount of glycerol derived from the non-reducing terminal glucose residue is detected.

(4) Partial hydrolysis of elsinan with dilute acid demonstrates that maltotriose, a small amount of maltotetraose, and other trisaccharides and tetrasaccharides containing both alpha-1,4 and alpha-1,3 linkages are present in the hydrolyzate.

The above observations, (1), (2), (3) and (4), show that the elsinan disclosed in the invention is a polysaccharide which is hardly branched and which comprises alpah-1,3 and alpha-1,4 linkages, with the main structure in which approx. three alpha-1,4-linked-glucose residues are repeatedly linked in alpha-1,3 fashion. In other words, the elsinan has an essentially linear-chain structure wherein maltotriose units are linked repeatedly in alpha-1,3 fashion. The observations, (2), (3) and (4), also show that although repeating units are predominantly maltotriose, maltotetraose residue is present in a small amount.

Consequently, elsinan is a novel glucan comprising repeating units of [3)-Glc-(1→4)-Glc-(1→4)-Glc-(1→].

The structure of elsinan can be illustrated as below.

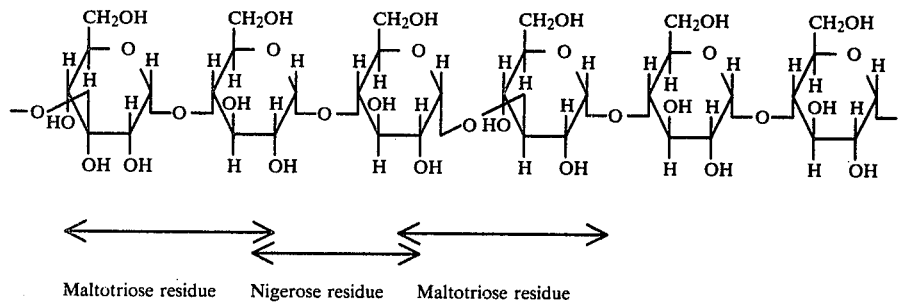

Maltotriose residue   Nigerose residue   Maltotriose residue

The mean molecular weight of elsinan is freely adjustable in the range of approx. 5,000 to approx. 10,000,000, because the glucan is producible by either chemical or biochemical procedure and is easily hydrolyzable with hydrochloric acid, sulfuric acid, etc.

The production of the elsinan disclosed in the invention is attainable by utilizing microorganisms of genus Elsinoe.

For example, *Elsinoe leucospila* is employable for the effective production of the elsinan. The microorganism was reported by Jenkins, A. E. et al in *Arq. Inst. Biol. S. Paulo*, no. 17, pp.67–72 (1946) and by Shigeo Takaya, et al in *Study of Tea*, no. 49, pp. 79–88 (1975) and deposited by the present inventors to the Fermentation Institute, Agency of Industrial Science and Technology, 8-1, 5-chome, Inagehigashi, Chiba, Japan. as FERM-P No. 3874.

The following microorganisms of genus Elsinoe are also employable for the production of elsinan:

| | |
|---|---|
| *Elsinoe ampelina* | IFO 5263, IFO 6359 |
| *Elsinoe araliae* | IFO 6166, IFO 7162 |
| *Elsinoe fawcetti* | IFO 6442, IFO 8417, ATCC 13200 |
| *Elsime annonae* | ATCC 15027 |
| *Elsinoe corni* | ATCC 11189 |
| *Elsinoe heveae* | ATCC 12570 |
| *Elsinoe lepagei* | ATCC 13008 |
| *Elsinoe tiliae* | ATCC 24510 |

The process for producing elsinan will be described in further details. According to the present invention, elsinan is produced by cultivating above-mentioned microorganisms of genus Elsinoe on a nutrient medium containing at least one or more members of a group consisting of starch hydrolyzates, mannose, fructose, mannitol and xylose as sugar sources and separating and recovering the formed elsinan therefrom.

Any starch hydrolyzates are employable as sugar sources for the nutrient medium in the invention. For example, single compounds such as glucose, maltose, maltotriose or maltotetraose, or combinations thereof, or partial starch hydrolyzates containing at least one of these compounds are employable.

Partial starch hydrolyzates include acid and/or amylase-conversion starch syrup or starch syrup solid with a desirable degree of hydrolysis. Partial starch hydrolyzates with a degree of hydrolysis of 5 or more, preferably, 10 or more, (Dextrose Equivalent: hereinafter, referred to as DE ) are suitable for producing the elsinan disclosed in the invention.

Besides single compound, fructose, a sugar mixture of glucose and fructose obtained by isomerization of glucose, a sugar mixture obtained by partial or complete inversion of sucrose, and date extract containing a mixture of glucose and fructose may be effectively used as the sugar source for the nutrient medium in the invention. Not only mannitol, a single compound, but also a sugar mixture of mannitol and sorbitol obtained by hydrogenation of fructose may be effectively used as sugar source.

Similarly, single compound, xylose, and sugar mixture of xylose, arabinose, galactose, mannose, etc. obtained from conversion of agricultural residues such as corn cob, bagasse, cotton seed hull, and rice or wheat stalk, or from conversion of wood may be effectively used for the purpose.

Synthetic compounds such as nitrates, ammonium salts, urea, and natural organic substances such as polypeptone, corn steep liquor, yeast extract, defatted soybean extract, peptides, amino acids may be used freely as nitrogen sources in the invention.

Phosphates, potassium salts, sulfates, and magnesium salts may be used freely as minerals. If necessary, other minerals such as ferrites or ferrates, calcium salts and manganates are also employable.

A culture medium may be in solid or liquid form. In the case of liquid medium, although static culture is also feasible, shaking culture or submerged culture results in a higher yield of elsinan. The concentration of the sugar sources should be 0.5–15 w/v %, and is preferably between 1–10 w/v % in the liquid culture medium.

The initial pH of the culture medium should be in the range that favors microbial growth and elsinan production. Generally, 5–8 is preferable. Similarly, the cultivation temperature should be in the range that favors the microbial growth and elsinan production. Generally, 20°–30° C. is preferable. Cultivation is carried out until a maximum yield of elsinan is obtained, generally, 3–7 days.

The resultant cultural broth wherein elsinan is produced and accumulated in accordance with the above-mentioned procedure exhibits high viscosity. The broth is treated by suitable procedures such as filtration or centrifugation to remove the cells and mycelia, and the elsinan in the thus-obtained clear filtrate or supernatant precipitates in a white plumage or gum form by the addition of appropriate precipitants, for example, organic precipitants such as methanol, ethanol, isopropanol and acetone. The elsinan is recovered by suitable procedures such as filtration or centrifugation. The resultant elsinan as such may be used as the finished product, or, the elsinan may be used after further purification by dissolving in water and effecting precipitation repeatedly by the addition of organic precipitants and, if necessary, drying. Any procedures such as through flow drying, hot air drying, spray drying, drum drying, vacuum drying and lyophilizing are applicable for the drying.

The processes for producing elsinan are illustrated by the following examples which are not intended to restrict the invention.

EXAMPLE 1

A liquid medium, consisting of 5 w/v % glucose, 0.5 w/v % defatted soybean, 0.042 w/v % $Na_2HPO_4$, 0.018 w/v % $KH_2PO_4$, and water, was sterilized at 120° C. for 20 minutes and then cooled. Thereafter, the medium was inoculated with *Elsinoe leucospila* FERM-P No. 3874 at an initial pH of 6.8 and subjected to submerged culture at 24° C. for five days.

After pasteurizing the resultant cultural broth at 85° C. for 15 minutes, the broth was subjected to centrifugation (5,000 g 20 minutes) to remove the cells and mycelia therefrom. Crude elsinan was obtained as a precipitate in a white plumage or gum form with the addition of 1.5 volumes of ethanol to the thus-obtained clear supernatant.

The crude elsinan was dissolved in water and subjected to centrifugation to remove insoluble substances, as described above, and then precipitation was effected by adding, ethanol again to the supernatant. After the procedure was repeated three times, the precipitate was lyophilized. White powder of purified elsinan was obtained at an approx. 60% (dry solid basis: hereinafter, referred to as d.s.b.) yield against the sucrose used in the medium.

Figure 2:
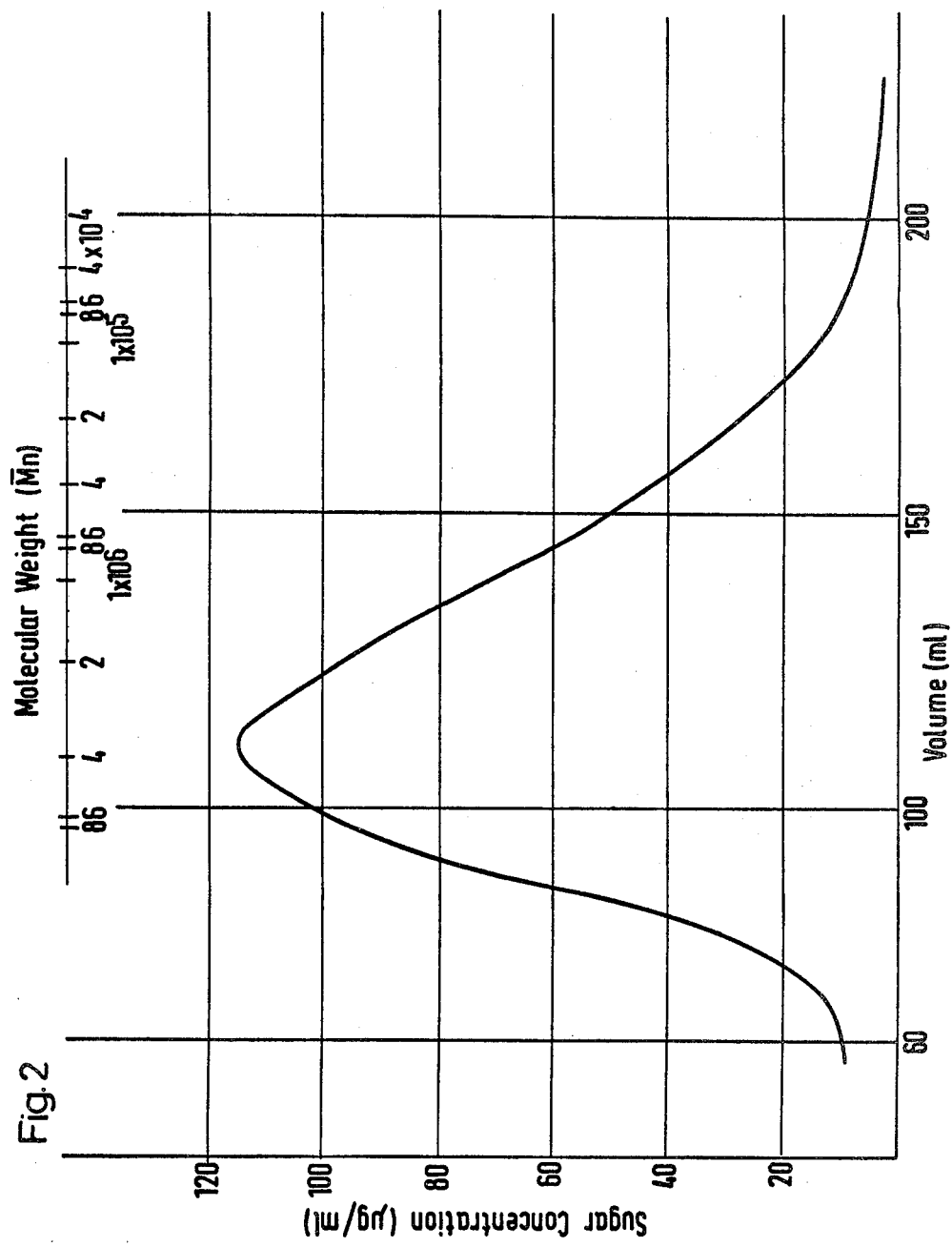
FIG. 2 shows the molecular weight distribution of the purified elsinan by the gel filtration method.

The viscosity of a 3 w/w % aqueous solution of the purified elsinan determined at 30° C., using Brookfield rotational viscometer, was 380 cps. The estimation of molecular weight distribution of the purified elsinan by the gel filtration method gave a distribution range from approx. 10,000 to approx. 10,000,000 or more, as illustrated in FIG. 2.

A 5 w/w % aqueous solution of the purified elsinan was casted uniformly on a clear glass plate and air-dried. A colorless, clear, intensive, flexible and self-supporting film was formed. The excellent film formability of elsinan leads to the applications as packaging film material and coating agent.

EXAMPLE 2

A liquid medium, consisting of 5 w/v % mannose, 0.5 w/v % corn steep liquor, 0.1 w/v % $K_2HPO_4$, 0.05 w/v % $MgSO_4, 7H_2O$, 0.05 w/v % KCl, 0.001 w/v % $FeSO_4, 7H_2O$ and water, was sterilized at 120° C. for 20 minutes and then cooled. Thereafter, the medium was inoculated with *Elsinoe araliae* IFO 6166 at an initial pH of 7.0 and subjected to submerged culture at 24° C. for six days.

The resultant cultural broth was treated similarly as described in Example 1 and purified elsinan (white powder) was obtained at an approx. 40% (d.s.b) yield against the mannose used in the medium.

EXAMPLE 3

A liquid medium, consisting of 3 w/v % partial starch hydrolyzate (starch syrup solid with a DE of 30), 0.3 w/v % wheat germ, 0.1 w/v % $NH_4NO_3$, 0.1 w/v % $K_2HPO_4$, 0.05 w/v % $MgSO_4.7H_2O$, 0.05 w/v % KCl, 0.0001 w/v % $MnSO_4.4H_2O$ and water, was sterilized at 120° C. for 20 minutes and then cooled. Thereafter, the medium was inoculated with *Elsinoe fawcetti* IFO 8417 at an initial ph of 6.0 and subjected to submerged culture at 28° C. for four days.

The resultant cultural broth was treated similarly as described in Example 1, and purified elsinan (white powder) was obtained at an approx. 70% (d.s.b.) yield against the partial starch hydrolyzate used in the medium.

EXAMPLE 4

A sterilized medium, consisting of the same ingredients as used in Example 1, except that 6 w/v % partial starch hydrolyzate (starch syrup with a DE of 60 and a moisture of 25%) was used instead of 5 w/v % glucose, was inoculated with *Elsinoe leucospila* FERM-P No. 3874 and cultivated similarly as described in Example 1.

The resultant cultural broth was treated similarly as described in Example 1, and purified elsinan (white powder) was obtained at an approx. 60% (d.s.b.) yield against the partial starch hydrolyzate used in the medium.

EXAMPLE 5

A sterilized medium, consisting of the same ingredients as used in Example 2 except that 5 w/v % maltose was used instead of 5 w/v % mannose, was inoculated with *Elsinoe alariae* IFO 6166 and cultivated similarly as described in Example 2.

The resultant cultural broth was treated similarly as described in Example 1, and purified elsinan (white powder) was obtained at an approx. 50% (d.s.b.) yield against the maltose used in the medium.

EXAMPLE 6

A sterilized medium, consisting of the same ingredients as used in Example 3 except that 5 w/v % isomerized sugar (sugar composition: glucose, 60%; fructose, 40%; a moisture of 25%) was used instead of 3 w/v % partial starch hydrolyzate, was inoculated with *Elsinoe fawcetti* IFO 8417 and subjected to submerged culture at 24° C. for five days.

The resultant cultural broth was treated similarly as described in Example 1, and purified elsinan (white powder) was obtained at an approx. 65% (d.s.b.) yield against the isomerized sugar used in the medium.

EXAMPLE 7

A sterilized medium, consisting of the same ingredients as used in Example 6 except that 3 w/v % partial inverted sugar (sugar composition: glucose, 20%; fructose, 20%; sucrose, 60%; a moisture of 25%) was used instead of 5 w/v % isomerized sugar, was inoculated with *Elsinoe fawetti* IFO 8417 and cultivated similarly as described in Example 6.

The resultant cultural broth was treated similarly as described in Example 1, and purified elsinan (white powder) was obtained at an approx. 65% (d.s.b.) yield against the partial inverted sugar used in the medium.

EXAMPLE 8

A liquid medium, consisting of 3 w/v % mannitol, 0.5 w/v % corn steep liquor, 0.1 w/v % $K_2HPO_4$, 0.05 w/v % $MgSO_4.7H_2O$, 0.05 w/v % KCl, 0.001 w/v % $FeSO_4.7H_2O$ and water, was sterilized at 120° C. for 20 minutes and then cooled. Thereafter, the medium was inoculated with *Elsinoe leucospila* FERM-P no. 3874 at an initial pH of 7.0 and subjected to submerged culture at 24° C. for six days.

The resultant cultural broth was treated similarly as described in Example 1, and purified elsinan (white powder) was obtained at an approx. 60% (d.s.b.) yield against the mannitol used in the medium.

EXAMPLE 9

A liquid medium, consisting of 5 w/v % xylose, 0.3 w/v % wheat germ, 0.1 w/v % NH$_4$NO$_3$, 0.1 w/v % K$_2$HPO$_4$, 0.05 w/v % MgSO$_4$.7H$_2$O, w/v % KCl, 0.0001 w/v % MnSO$_4$.4H$_2$O and water, was sterilized at 120° C. for 20 minutes, and then cooled. Thereafter, the medium was inoculated with *Elsinoe fawcetti* IFO 8417 at an initial pH of 6.0 and subjected to submerged culture at 28° C. for four days.

The resultant cultural broth was treated as described in Example 1, and purified elsinan (white powder) was obtained at an approx. 40% (d.s.b.) yield against the xylose used in the medium.

What is claimed is:

1. A process for producing elsinan, a glucan consisting essentially of repeating units of [3)-Glc-(1→4)-Glc-(1→4)-Glc-(1→], (wherein Glc represents α-D-glucopyranose residue), comprising cultivating microorganisms of genus Elsinoe capable of producing said elsinan, on a nutrient medium containing a carbon source selected from the group consisting of starch hydrolyzates, mannose, fructose, mannitol, xylose, and mixtures thereof, to produce the elsinan, and separating and recovering said elsinan.

2. A process in accordance with claim 1 wherein said microorganisms are of a species selected from the group consisting of:

| *Elsinoe leucospila* | FERM-P No. 3874 |
|---|---|
| *Elsonoe ampelina* | IFO 5263 |
| *Elsinoe ampelina* | IFO 6359 |
| *Elsinoe araliae* | IFO 6166 |
| *Elsinoe araliae* | IFO 7162 |
| *Elsinoe fawcetti* | IFO 6442 |
| *Elsinoe fawcetti* | IFO 8417 |
| *Elsinoe fawcetti* | ATCC 13200 |
| *Elsinoe annonae* | ATCC 15027 |
| *Elsinoe corni* | ATCC 11189 |
| *Elsinoe heveae* | ATCC 12570 |
| *Elsinoe lepagei* | ATCC 13008, and |
| *Elsinoe tiliae* | ATCC 24510. |

* * * * *